(12) United States Patent
Kraetschmer et al.

(10) Patent No.: US 8,849,425 B2
(45) Date of Patent: Sep. 30, 2014

(54) IMPLANTABLE APPARATUS FOR DETECTION OF EXTERNAL NOISE USING MOTION SENSOR SIGNAL

(75) Inventors: Hannes Kraetschmer, West Linn, OR (US); Dirk Muessig, West Linn, OR (US); Jeffrey A. Von Arx, Lake Oswego, OR (US); Larry Stotts, Tigard, OR (US)

(73) Assignee: Biotronik SE & Co. KG, Berlin (DE)

( * ) Notice: Subject to any disclaimer, the term of this patent is extended or adjusted under 35 U.S.C. 154(b) by 174 days.

(21) Appl. No.: 13/455,136

(22) Filed: Apr. 25, 2012

(65) Prior Publication Data

US 2012/0283544 A1 Nov. 8, 2012

Related U.S. Application Data

(60) Provisional application No. 61/481,756, filed on May 3, 2011.

(51) Int. Cl.
| | |
|---|---|
| *A61N 1/00* | (2006.01) |
| *A61B 5/11* | (2006.01) |
| *A61N 1/05* | (2006.01) |
| *A61B 5/00* | (2006.01) |
| *A61B 5/024* | (2006.01) |
| *A61B 5/0452* | (2006.01) |
| *A61B 5/04* | (2006.01) |

(52) U.S. Cl.
CPC ............... *A61N 1/0504* (2013.01); *A61B 5/11* (2013.01); *A61B 5/6867* (2013.01); *A61B 5/721* (2013.01); *A61B 5/686* (2013.01); *A61B 5/02405* (2013.01); *A61B 2562/0219* (2013.01); *A61B 5/0452* (2013.01)
USPC ............ 607/122; 600/373; 600/377; 607/119

(58) Field of Classification Search
CPC ..... A61N 1/0488; A61N 1/05; A61N 1/3684; A61B 5/0031
USPC ......... 600/372–375, 377, 381, 393, 587, 595; 607/115–116, 119, 122–123
See application file for complete search history.

(56) References Cited

U.S. PATENT DOCUMENTS 5,941,904 A * 8/1999 Johnston et al. ................ 607/19
6,347,245 B1 2/2002 Lee et al.

(Continued)

FOREIGN PATENT DOCUMENTS

WO 2008/137536 A1 11/2008

OTHER PUBLICATIONS

European Search Report, dated Aug. 13, 2012, 7 pages.

*Primary Examiner* — Linda Dvorak
*Assistant Examiner* — Brian M Antiskay
(74) *Attorney, Agent, or Firm* — ARC IP Law, PC; Joseph J. Mayo (57) ABSTRACT

Detects external noise using a motion sensor signal for example to increase the specificity of arrhythmia detections based on active muscle noise detection. Whenever a motion signal is present that is below or above a certain frequency, for example 5 Hz, or within a certain frequency range, for example 1 to 10 Hz, and/or above a certain amplitude, for example greater than 1 mg, or close to a known motion pattern, then the detection of fast ventricular arrhythmia is suspended. For the detection of slow arrhythmia, for example asystole or syncope, an episode is confirmed when a short lasting motion sensor signal occurs. Uses a motion sensor based signal, for example as obtained from an accelerometer on an implantable electrode lead and/or implantable device.

19 Claims, 5 Drawing Sheets

(56) References Cited

U.S. PATENT DOCUMENTS

| | | |
|---|---|---|
| 6,714,806 B2 * | 3/2004 | Iaizzo et al. .................. 600/374 |
| 8,326,419 B2 * | 12/2012 | Rosenberg et al. ............... 607/9 |
| 2002/0035381 A1 * | 3/2002 | Bardy et al. ...................... 607/4 |
| 2006/0241521 A1 | 10/2006 | Cohen |
| 2010/0312131 A1 | 12/2010 | Naware et al. |
| 2012/0143031 A1 * | 6/2012 | Belalcazar et al. ........... 600/377 |

* cited by examiner

IMPLANTABLE APPARATUS FOR DETECTION OF EXTERNAL NOISE USING MOTION SENSOR SIGNAL

This application claims the benefit of U.S. Provisional Patent Application 61/481,756, filed on 3 May 2011, the specification of which is hereby incorporated herein by reference.

BACKGROUND OF THE INVENTION

1. Field of the Invention

Embodiments of the invention relate to a method to detect external noise using a motion sensor signal for example to increase the specificity of arrhythmia detections based on active muscle noise detection, specifically and not by way of limitation, embodiments improve the specificity of the arrhythmia detection by active detection of lead or device movement associated with electromedical implants. The electromedical implant can, for example, be an appropriately configured implantable loop recorder or ILR for long terming monitoring of electrocardiograms or ECGs or other implantable pacemaker or an implantable cardioverter/defibrillator or ICD, or any combination thereof.

2. Description of the Related Art

The primary purpose of implantable loop recorders or ILRs is the detection and/or monitoring of cardiac arrhythmia such as ventricular tachycardia or VT, atrial tachycardia or AT, ventricular fibrillation or VF, or asystole or syncope. The detection of these types of arrhythmia episodes is often impaired by cardiac unrelated disturbances such as muscle movement related noise and/or external noise. Due to these types of noise, the evaluation and/or analysis of the subcutaneous electrocardiogram or SECG with respect to detection of arrhythmia episodes is often mislead and unspecific. For example, arm movement leads to muscle noise, which is detected as a high frequent signal and potentially recognized as VT. Another example is the false detection of syncope due to under sensing of low amplitude SECG.

Currently, ILRs are sensitive in detecting arrhythmia but not very specific, i.e., are subject to a high number of false positives. These false detections introduce inefficiencies with respect to post analysis logistical efforts to schedule patient visits and significantly impair the diagnostic use of ILRs. Some studies show that overall specificity of ILRs is about 15% and even worse for high ventricular rates where specificity of ILR's drops to 0.3%.

BRIEF SUMMARY OF THE INVENTION

At least one embodiments of the invention utilizes a motion sensor based signal to increase the specificity of arrhythmia detections, for example as analyzed in combination with an sECG. Whenever a motion signal is present, for example over a threshold for time and/or amplitude, the detection of fast arrhythmia is suspended in one or more embodiments of the invention. For the detection of slow arrhythmia, for example asystole or syncope, an episode is confirmed when a short lasting motion sensor signal occurs in one or more embodiments. For example, at least one embodiment of the invention combines multiple signals to correctly discriminate arrhythmia from external noise or low amplitude SECG signals. The method uses the motion sensor based signal, for example as obtained from an accelerometer on an implantable electrode lead and/or implantable device, to increase the specificity of arrhythmia detections. In one or more threshold comparison embodiments, whenever a motion signal is present that is below or above a certain frequency, for example 5 Hz, or within a certain frequency range, for example 1 to 10 Hz, and/or above a certain amplitude, for example greater than 1 mg, then the detection of fast ventricular arrhythmia is suspended. In addition, in one or more embodiments, for the detection of slow arrhythmia (asystole, syncope), an episode is confirmed when a short lasting or short duration motion sensor signal occurs.

In one exemplary embodiment, an implantable medical device in a hermetically sealed housing implements an embodiment of the invention and includes electrodes to sense cardiac signals, signal analysis element to process the sensed cardiac signals that may for example include amplifiers, analog/digital converters and the like, a detection element to detect cardiac arrhythmias, a comparison or processing element, along with a memory, at least one motion sensor, a power source and an optional telemetry element. The electrodes in one or more embodiments may be implemented with one or more electrode leads that include electrode contacts, as is known in the art of pacemakers for example. In another embodiment, the electrodes are located at or part of the housing. In yet another embodiment, electrodes at an electrode lead and at the housing are used. The motion sensor may be implemented with an acceleration sensor, such as a microelectromechanical or MEMS format accelerometer as known in the art. Small-scale accelerometers may also include gyroscopes for angular rotation determination and use of rotational information is in keeping with the spirit of the invention, whether derived from differencing of two accelerometer vectors or through use of one or more gyroscopes. Suitable acceleration sensors are sensors that detect acceleration in at least one axis or acceleration in multiple movement axes. Calibration of the orientation may be performed after implantation via the optional telemetry unit with the patient lying face up or face down, on one or each side and standing. Once the orientation of the accelerometers in the body is determined, then the patient may be instructed to move the arms and/or legs or other perform other muscle movements that may be detected by the accelerometer or accelerometers and for example saved in memory for later pattern comparison. The stored patterns of movement may be compared with the detected accelerometer values to determine whether to mark an arrhythmia as incorrect or as confirmed in one or more embodiments in addition to the threshold comparisons previously described.

Arrhythmia detection of the cardiac signal is performed in any manner, for example based on timing or other analysis of peaks or signal markers or features observed in the sECG as one skilled in the art will appreciate. The signal of the motion sensor is processed to detect motion signal features. Motion signal features may include amplitude, frequency, signal polarity, waveform or the like or the may be detected or otherwise identified by comparison with recorded reference signals, for example previously stored patterns. The motion sensor signals may be analog or digital depending on the specific embodiment of the accelerometer utilized. Once an arrhythmia is detected the motion signal features detected prior and/or during the arrhythmia are analyzed. Depending on the motion signal features, the detected arrhythmia is either marked as incorrect or confirmed.

BRIEF DESCRIPTION OF THE DRAWINGS

FIG. 4: illustrates a logical processing schematic of one embodiment of the signal analysis element or module employed by one or more embodiments of the invention. The signal or data streams from the accelerometer and the sECG, are routed into detection modules that generate peak markers or detect signal features from the sECG and signal frequencies/amplitudes or other motion related characteristics from the accelerometer(s). The arrhythmia detection element analyzes the times of the various peaks in one or more embodiments to recognize potential arrhythmia. The time sequence of the peak markers or signal features of the potential arrhythmia are compared to the time sequence of motion related characteristics in the comparator element or module, which marks the arrhythmia as incorrect or confirmed based on the motion related characteristics.

DETAILED DESCRIPTION OF THE INVENTION

Figure 1:
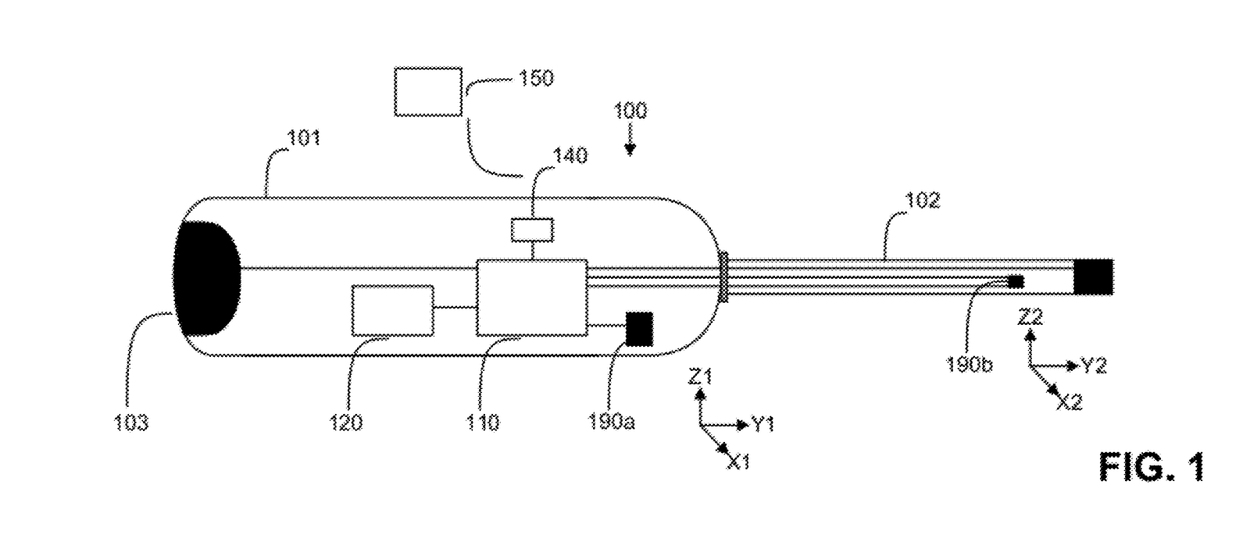
FIG. 1: illustrates an ILR having a device body and a flexible lead and showing the orientation axes associated with each accelerometer.

FIG. 1 illustrates an embodiment of the invention 100 implemented with an ILR having device body 101 and flexible lead body 102 and at least one accelerometer 190$a$ and/or 190$b$. In at least one embodiment, the implantable medical device includes a hermetically sealed housing implementation of device body 101 and includes signal analysis element 110 to process the sensed cardiac signals that may for example include amplifiers, analog/digital converters and the like, a detection element to detect cardiac arrhythmias, a comparison or processing element as shown in further detail in FIG. 4, along with memory 120, a power source which is not shown for brevity, and an optional telemetry element 140. The telemetry element for example may be configured to communicate with remote device programmer 150 or any other remote computing element as desired.

One or more embodiments may utilize an accelerometer in device body 101 or in flexible lead body 102 or in both locations. Also shown next to each accelerometer is a respective reference frame (X1, Y1 and Z1) and (X2, Y2 and Z2) respectively, that each accelerometer may be calibrated to after implantation when the ILR and flexible lead body are set in a given orientation. Signals originating in flexible lead body 102, for example electrical signals, enter device body 101 and are processed by signal analysis module 110 and generally a digitized subset thereof may be stored in memory 120, along with analysis results, arrhythmia detections and/or false arrhythmia detections, or they may be ignored for example. In addition, motion related characteristics from accelerometer 190$a$ and/or 190$b$ may be stored in memory, for example to aid in determining how much exercise or other movement a patient undergoes over time. Embodiments may also store potential arrhythmia events in memory along with associated motion characteristics for later analysis to determine what types of motions result in false positives. In one or more embodiments of the invention, the time of day may also be stored in order to determine if arrhythmia or false positives thereof occur more often in a particular time of day. If false positives occur more often in a particular time of the day, this may be taken into account when flagging potential arrhythmia or when marking potential arrhythmia as incorrect. In addition, if false positives occur more often in a given body orientation, this information may also be stored in memory and utilized in filtering potential arrhythmia. If actual arrhythmia occur in a particular body orientation more often, then the patient for example may be instructed to avoid that orientation, for example laying on a left side of the body. Embodiments of the invention may be implemented with any other type of implantable device as desired including pacemakers and/or cardioverter/defibrillators.

Before processing begins, and generally during implantation or during an office visit, the accelerometers may be calibrated for orientation, so that their particular orientations in the body of a patient are detected via a gravity vector of 1 g that is observed at a particular direction with respect to each accelerometer. Calibration of the orientation may be performed after implantation via the optional telemetry unit 140 and associated remote programming device 150 for example, with the patient lying face up or face down, on one or each side and/or standing. Alternatively, calibration of orientation may occur upon acceptance of physical gestures from the patient or attending physician as described further below.

For example, in one or more embodiments, the reference frame may be defined with respect to the body of the patient, with the y-axis pointing out the left side of the patient's body, the x-axis pointing out of the chest of the patient, and the z-axis point out of the top of the head of the patient. In addition, each accelerometer is assigned a device frame, with the x, y and z axes aligned however they are implanted. Generally, the accelerometer device x, y and z axes are assumed to be orthogonal, however as one skilled in the art will appreciate, this may be accounted for via another matrix transformation calibration step if required. To calibrate the orientation of the accelerometers, the gravity vector is utilized to find the mapping, or rotation matrix Q, between the device frame coordinates for each accelerometer and the patient's body frame coordinates. This calibration step in effect enables the recovery of orientation of each device inside the patient's body, post implantation. Each device accelerometer measures g in the respective device frame. Hence, if the patient is placed in a known orientation, then g in the patient's body frame is known. Although the patient may be oriented on the back, side and standing, by gathering information in two orientations, the other orientation may be derived from a cross product. Hence, with only two body positions, it is possible to calculate the full mapping between the frames of reference. For example, if the patient is placed on their stomach, then g [Body]=gi, wherein i is the x-axis unit vector. External programmer 150 for example may command the signal analysis element 110 for example to sample a three axes acceleration vector, or average one over a period of time for example to eliminate noise. In this case, accelerometer 190b may measure g [Device] and obtain three axes vector u. With the patient placed on their left side, g [Body]=gj, wherein j is the y-axis unit vector, at which time again, the external programmer commands the signal analysis element to sample another three axes acceleration vector, or average the vector for example. In this case, the accelerometer may measure g [Device] and obtain three axes vector v. The rotation matrix Q is utilized herein to denote the matrix that converts Device frame coordinates to Body frame coordinates. As such, Qu=gi and Qv=gj. As one skilled in the art will appreciate, using the cross product, (Qu×Qv)=Q(u×v), and hence Q(u×v)=gi×gj=gk, wherein k is the z-axis unit vector, enables the determination of the vertical translation. Thus with only two orientation measurements, it is possible to solve for the rotation matrix Q. For example, if Qinv is used to denote the inverse of Q, then (Qinv)i=(1/g)u, (Qinv)j=(1/g)v and (Qinv)k=(1/g)(u×v). Hence, Qinv is the matrix with columns (1/g)u, (1/g)v and (1/g)(u×v). Thus, by inverting Qinv, the rotational matrix Q is obtained and for example stored in memory 120 for each accelerometer.

Alternatively, for embodiments with or without telemetry units, the patient or attending physician may simply physically gesture to the implantable device to calibrate orientations. For example, in one or more embodiments of the invention, the patient or attending physician may physically tap the area of the body three times where the accelerometer is placed to indicate that the first position orientation should be sampled, for example when the patient is positioned with back oriented down. The patient may then stand up and tap the area of the body using the same gesture, for example three times in three seconds to indicate that the second orientation should be sampled. In this scenario, embodiments of the invention may calibrate orientation with or without a telemetry unit or external programmer through physical gestures. Feedback in the form of three small electric pulses to the electrode lead to tingle the area of the patient's body may be performed to inform the patient that the device orientation has been calibrated. The exemplary gestures are not intended to be limiting in any manner and any pattern of accelerations with respect to time may be utilized to signify that calibration should take place.

Figure 4:
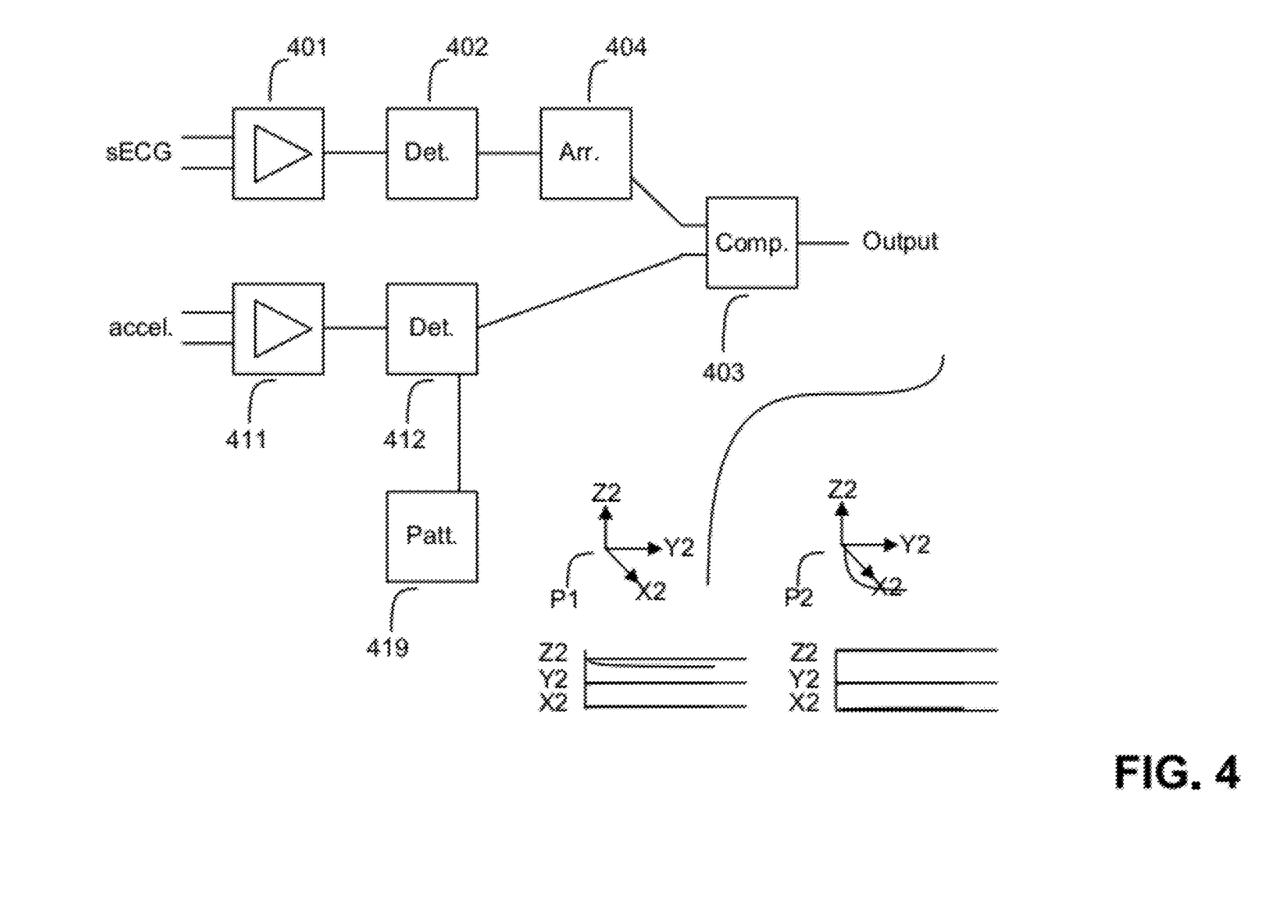

Once the orientation of the accelerometers in the body is determined and for example a rotation matrix is stored in memory 120 for each accelerometer, then the patient may optionally be instructed to move the arms and/or legs or other perform other muscle movements that may be detected by the accelerometer or accelerometers and for example saved in memory for later pattern comparison as shown in FIG. 4. The stored patterns of movement may be compared with the detected accelerometer values or motion characteristics to determine whether to mark an arrhythmia as incorrect or as confirmed in one or more embodiments in addition to the threshold comparisons for example.

With the initial orientation rotation matrices stored in memory, any incoming accelerometers values may be translated through a matrix multiply of the rotation matrix to obtain the true directional values according to the body frame of the patient. This enables statistics such as the percentage of time that a patient is lying down versus standing up to be correlated for false positives for example, to further improve the specificity of one or more embodiments of the invention by storing these and other derived motion characteristics for comparison and analysis. The analysis may be performed by the remote programming device, which may be implemented for example with a service center. In one or more embodiments of the invention, two or more accelerometers may be utilized and in this scenario, the patterns and/or motion characteristics from the two or more accelerometers may be compared to patterns in combination to more accurately recognize the current motion. Alternatively, or in combination, the acceleration vectors may be compared to one another or otherwise differenced to determine relative acceleration and to increase the specificity of arrhythmia detection for example while driving, flying and or accelerating or decelerating in any other environment.

Figure 2:
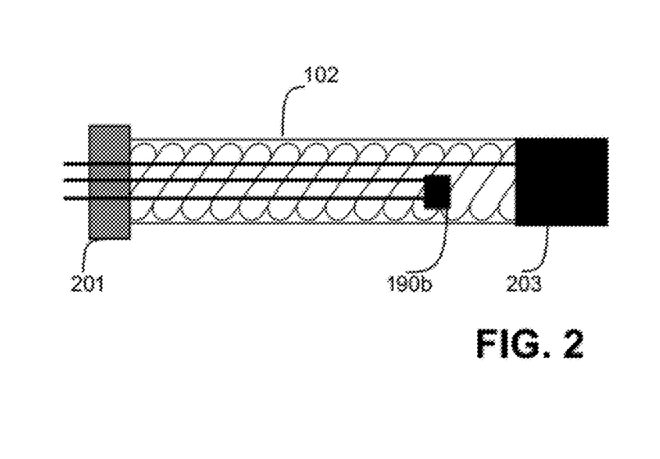
FIG. 2: illustrates a close-up of the flexible lead body having an accelerometer embedded into the lead body. The accelerometer is connected to the signal analysis module via a feedthrough. The feedthrough also connects the sECG electrode that is located at the distal end of the lead to the signal analysis module.

FIG. 2 illustrates a close-up of flexible lead body 102 having accelerometer 190b embedded within flexible lead body 102. Accelerometer 190b is connected to the signal analysis module 110 via feedthrough 201. Flexible lead body 102 also includes sECG electrode 203 that is also connected to signal analysis module 110 via feedthrough 201. The subcutaneous ECG signal or sECG is measured between one electrode at the tip of the lead, i.e., sECG electrode 203 and one electrode on the case on the opposite side of the device, i.e., device body electrode 103, shown as a filled half circle on the left side of device body 101. In alternative embodiments, sECG electrode 203 may be implemented as a tip electrode, wherein another ring electrode may be utilized to obtain the sECG instead of through use of the device body electrode if desired (not shown for brevity).

Figure 3:
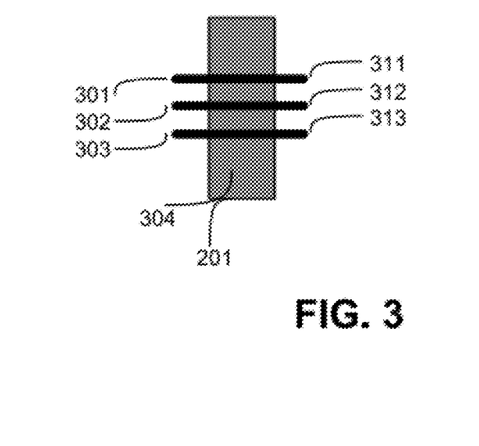
FIG. 3: illustrates a close-up of the feedthrough that provides electrical connection of the accelerometer and sECG lead to the signal analysis module.

FIG. 3 illustrates a close-up of feedthrough 201 that provides electrical connections 311, 312 and 313 on the flexible lead body side of feedthrough 201 to the sECG electrode 203 and accelerometer 190b common and positive respectively, to electrical connections 301, 302 and 303 through feedthrough body 304. Thus, feedthrough 201 enables the internal electronics of the ILR, such as signal analysis module 110 to obtain electrical signals that are generated external to the ILR. Modern accelerometers are very small and may be produced in different form factors, such as microelectromechanical of MEMS format. This results in a voltage generated by accelerometer and/or digital representation thereof.

FIG. 4 illustrates a logical processing schematic of one embodiment of signal analysis element or module 110 employed by one or more embodiments of the invention. The use of the terms element and module herein are interchangeable and otherwise synonymous and indicate any type of processing object that may include hardware, shared hardware in combination with or without firmware or software. Any type of element may be utilized so long as the element may detect, compare and indicate arrhythmia events within the required time between heartbeats, which requires minimal hardware and/or software complexity based on the relatively low rate of processing utilized as one skilled in the art will appreciate. In one or more embodiments of the invention, a single processing unit may implement all elements or modules or any combination thereof, for example by time division processing of the various signals and outputs.

The signal or data streams from the accelerometer and the sECG, i.e., the sECG signal and the accelerometer signal that travel on electrical connections 311 and 312/313 respectively, pass through feedthrough body 304 to electrical connections 301 and 302/303 respectively and are routed into optional amplifiers 401 and 411 respectively and to detection modules 402 and 412 respectively that generate peak markers or detect signal features and signal frequencies and/or amplitudes and motion characteristics from the accelerometer(s). The detected movement signal features or motion characteristics may include amplitude, signal polarity, waveform or the like or may be detected by comparison with recorded reference signals previously stored in memory for example. Patterns P1 and P2 show acceleration vectors as detected by a three axes accelerometer. Pattern P1 shows an upward acceleration in the Z axis and Y axis, indicative of an upward and outward movement of the arm near which the accelerometer is placed for example. Pattern P2 shows an outward and sideward acceleration indicative of a patient in the initial phase of reaching to the side. Both patterns are also shown with the three components of acceleration associated with each axis for example beneath the three-dimensional map for clarity. Comparison of current motion to known patterns may be made in detection module 412 and/or in or with a separate pattern element 419, either of which for example that calculate and/or access patterns previously stored in memory 120. Comparison of the current pattern of motion with a series of stored patterns may be performed by checking the peak amplitudes of the various vectors with respect to time and for example signifying a match if the amplitudes and directions match over a predefined percentage of time segments within any or all of the three axes for example. Any other pattern matching algorithm may be utilized in keeping with the spirit of the invention. Processing in detection modules 402 and 412 (or a single module that time division multiplexes processing for example) may be in the analog or digital domain as desired. Specifically, the time sequences of the sEGC markers are analyzed by arrhythmia detection module 404 and processed, or analyzed to find specific sequences that are indicative of different arrhythmias, for example by comparing event intervals within a sequence of events, or in any other manner as one skilled in the art will appreciate. The time sequence of the peak markers or signal features are of the potential arrhythmia are compared against times of motion events or patterns, and based on the values of various motion characteristics, comparator module 403 determines whether the arrhythmia is confirmed or incorrect.

Figure 5:
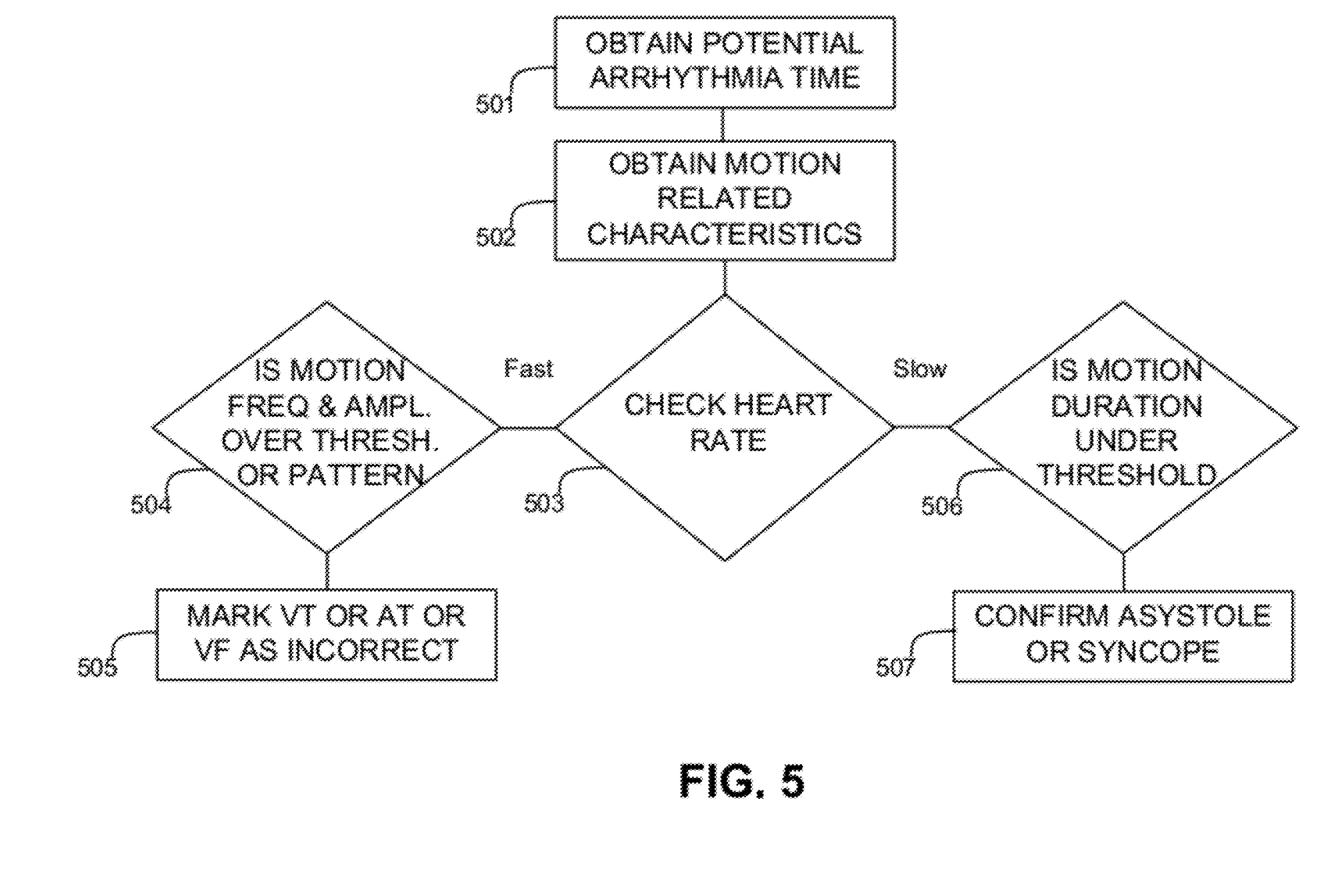
FIG. 5: illustrates a flow chart for an embodiment of the processing employed by the comparator element. The comparator element analyzes the time of the potential arrhythmia with respect to the motion related characteristics, for example frequency/amplitude/duration and/or pattern and based on the detected heart rate, marks the arrhythmia as incorrect or confirmed.

FIG. 5 illustrates a flow chart for an embodiment of the processing employed by the comparator element. The comparator element obtains the time of the potential arrhythmia at 501 and obtains motion related characteristics, for example frequency/amplitude/duration and/or pattern at 502. If the detected heart rate as determined at 503 is fast, then the motion related characteristics are compared to threshold(s) such as frequency/amplitude and/or a pattern at 504 to determine if the motion related characteristics are over threshold and/or a known pattern of movement. If so, the arrhythmia is marked as incorrect, otherwise the arrhythmia is marked as confirmed at 505. If on the other hand the heart rate is beneath a particular predefined rate, for example under 60 beats per minute, then if the duration of the motion characteristic is beneath a predefined duration as determined at 506, then the arrhythmia is confirmed at 507, otherwise the arrhythmia is marked as incorrect.

Figure 6:
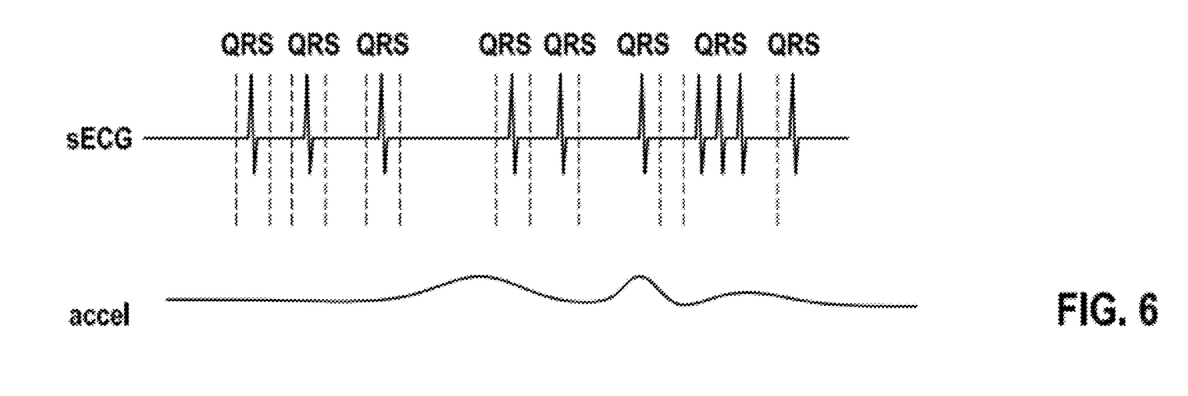
FIG. 6: illustrates an example of correct arrhythmia detection, wherein the sECG signal indicates an arrhythmia and the motion sensor indicates below threshold motion as determined from either frequency or amplitude or both or any other motion related characteristic.

FIG. 6 illustrates an example of correct arrhythmia detection, wherein the sECG signal indicates an arrhythmia and the motion sensor indicates below threshold motion as determined from either frequency or amplitude or both or any other motion related characteristic.

Figure 7:
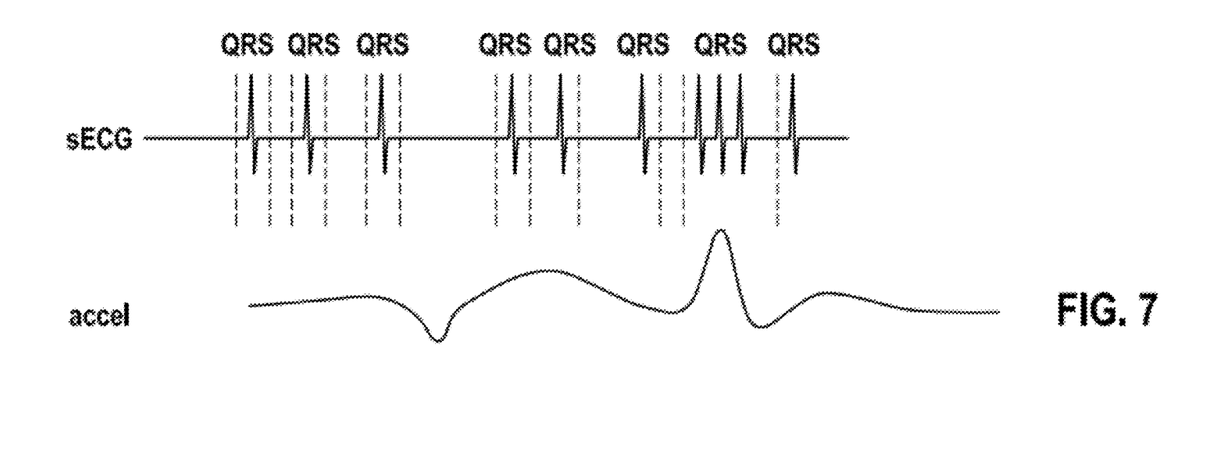
FIG. 7: illustrates an example of incorrect arrhythmia detection, wherein the sECG signal indicates an arrhythmia and the motion sensor indicates above threshold motion as determined from either frequency or amplitude or both or any other motion related characteristic.

FIG. 7 illustrates an example of incorrect arrhythmia detection, wherein the sECG signal indicates an arrhythmia and the motion sensor indicates above threshold motion as determined from either frequency or amplitude or both or any other motion related characteristic.

Figure 8:
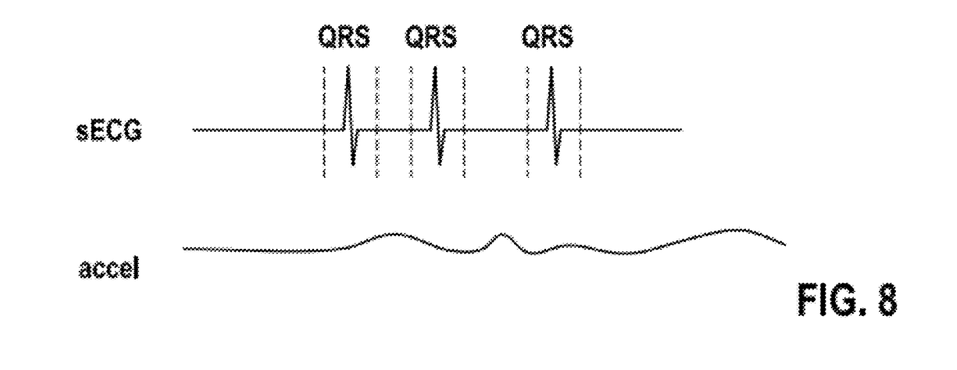
FIG. 8: illustrates an example of confirmed arrhythmia detection, wherein the sECG signal indicates an asystole or syncope and the motion sensor indicates a short duration motion related characteristic.

FIG. 8 illustrates an example of confirmed arrhythmia detection, wherein the sECG signal indicates an asystole or syncope and the motion sensor indicates a short duration motion related characteristic.

Figure 9:
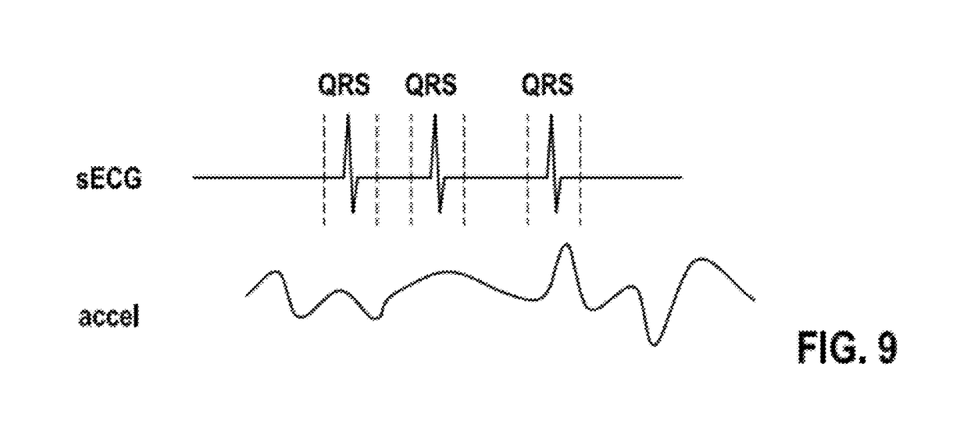
FIG. 9: illustrates an example of incorrect arrhythmia detection, wherein the sECG signal indicates an asystole or syncope and the motion sensor does not indicate a short duration motion related characteristic.

FIG. 9 illustrates an example of incorrect arrhythmia detection, wherein the sECG signal indicates an asystole or syncope and the motion sensor does not indicate a short duration motion related characteristic. In this manner, embodiments of the invention enable high arrhythmia detection specificities through the elimination of false positives associated with muscle movement.

What is claimed is:

1. An implantable apparatus configured to detect external noise comprising:
    a device body comprising
        a signal analysis element coupled with a device body electrode;
        a memory coupled with said signal analysis element;
    a flexible lead body comprising
        a proximal end;
        a distal end;
        at least one electrode situated proximally to said distal end of said flexible lead body wherein said at least one electrode is coupled with said signal analysis element;
    at least one accelerometer coupled with said signal analysis element;
        wherein each of said at least one accelerometer comprises device frame coordinates;
    said signal analysis element comprising
        at least one detection element configured to detect peak markers or signal features from said at least one electrode that is implanted in a body of a patient and at least one motion characteristic from said at least one accelerometer that is also implanted in said body of said patient;
        wherein said signal analysis element is configured to:
            determine if a potential arrhythmia condition exists based on said peak markers or said signal features; and
            obtain a heart rate from said peak markers or said signal features; and
            obtain said at least one motion characteristic from said at least one detection element; and
            determine if said peak markers or said signal features from said at least one electrode occur in a time window that includes said at least one motion characteristic over at least one threshold for frequency or amplitude or frequency and amplitude or within range of a pattern if said heart rate is above a fast threshold and if so, mark said potential arrhythmia as incorrect, or otherwise mark said potential arrhythmia as confirmed
            or
            determine if said at least one motion characteristic is under a duration threshold if said heart rate is below a slow threshold and if so, mark said potential arrhythmia as confirmed, or otherwise mark said potential arrhythmia as incorrect; and
        obtain a first sample orientation associated with a first body position of said patient and obtain at least a second sample orientation associated with a second body position of said patient; and
        calculate patient body frame coordinates of said body of said patient from said first sample orientation and said second sample orientation; and calibrate said at least one accelerometer to said device frame coordinates of each of said at least one accelerometer and said patient body frame coordinates; and, calculate a rotation matrix between said device frame coordinates of each of said at least one accelerometer and said patient body frame coordinates to calibrate said at least one accelerometer.

2. The implantable apparatus of claim 1 wherein said at least one accelerometer is coupled with said flexible lead body.

3. The implantable apparatus of claim 1 wherein said at least one accelerometer is coupled with said device body.

4. The implantable apparatus of claim 1 wherein said at least one accelerometer comprises a plurality of accelerometers coupled with said flexible lead body and device body respectively.

5. The implantable apparatus of claim 1 wherein said at least one accelerometer comprises a first accelerometer coupled with said flexible lead body and a second accelerometer coupled with said device body respectively and wherein said signal analysis element is configured to obtain a difference between a first acceleration vector from said first accelerometer and a second acceleration vector from said second accelerometer and determine a net acceleration and utilize said net acceleration as said motion characteristic.

6. The implantable apparatus of claim 1 wherein said signal analysis element further comprises
at least one arrhythmia element coupled with a detection element associated with said at least one electrode; and,
a comparator element coupled with said at least one arrhythmia element and said at least one detection element that is configured to detect said at least one motion characteristic.

7. The implantable apparatus of claim 1 wherein said signal analysis element further comprises:
a pattern processing element configured to compare a previously stored pattern of motion with said at least one motion characteristic and identify a particular type of motion from said at least one motion characteristic.

8. The implantable apparatus of claim 1 further comprising a telemetry unit coupled with said signal analysis element wherein said telemetry unit is configured to communicate with a remote device.

9. The implantable apparatus of claim 8 wherein said signal analysis element is further configured to store orientation sample acceleration vectors for different body positions of said patient after receipt of commands from said remote device.

10. The implantable apparatus of claim 1 wherein said signal analysis element is further configured to store orientation sample acceleration vectors for different body positions of said patient, after receipt of physical gestures on said body of said patient at a location of said at least one accelerometer, to calibrate said at least one accelerometer.

11. The implantable apparatus of claim 1 wherein said signal analysis element is further configured to store incorrect or confirmed or both incorrect and confirmed arrhythmia events in said memory along with said at least one motion characteristic for later analysis.

12. The implantable apparatus of claim 1 wherein said signal analysis element is further configured to store incorrect or confirmed or both incorrect and confirmed arrhythmia events in said memory along with said at least one motion characteristic and a time of day for later analysis.

13. The implantable apparatus of claim 1 wherein signal analysis element is further configured to store said at least one rotation matrix in said memory wherein each of said at least one rotation matrix is associated with said at least one accelerometer respectively.

14. The implantable apparatus of claim 1 wherein signal analysis element is further configured to obtain said at least one rotation matrix from said memory wherein each of said at least one rotation matrix is associated with said at least one accelerometer respectively and convert incoming acceleration vectors into a reference frame associated with said body of said patient.

15. The implantable apparatus of claim 1 wherein said device body further comprises a device body electrode wherein said at least one detection element is further configured to detect a voltage differential between said at least one electrode and said device body electrode.

16. The implantable apparatus of claim 1 wherein said signal analysis element comprises at least one amplifier coupled with said at least one detection element wherein said at least one amplifier is configured to amplify input voltages from said at least one electrode or said at least one accelerometer or from said at least one electrode and said at least one accelerometer.

17. The implantable apparatus of claim 1 further comprising:
a feedthrough configured to physically couple with said device body and said flexible lead body and
electrically couple said at least one electrode to said signal analysis element and
electrically couple said at least one accelerometer to said signal analysis element.

18. The implantable apparatus of claim 1 wherein said electromedical implant comprises
an implantable loop recorder or
an implantable pacemaker or
an implantable cardioverter/defibrillator.

19. An implantable apparatus configured to detect external noise comprising:
a device body comprising
a signal analysis element coupled with a device body electrode;
a memory coupled with said signal analysis element;
an flexible lead body comprising
a proximal end;
a distal end;
at least one electrode situated proximally to said distal end of said flexible lead body wherein said at least one electrode is coupled with said signal analysis element;
at least one accelerometer coupled with said signal analysis element;
wherein each of said at least one accelerometer comprises device frame coordinates;
said signal analysis element comprising
at least one detection element configured to detect peak markers or signal features from said at least one electrode that is implanted in a body of a patient and at least one motion characteristic from said at least one accelerometer that is also implanted in said body of said patient;
wherein said signal analysis element is configured to:
obtain a first sample orientation associated with a first body position of said patient and obtain at least a second sample orientation associated with a second body position of said patient; and
calculate patient body frame coordinates of said body of said patient from said first sample orientation and said second sample orientation; and calculate at least one rotation matrix between said device frame coordinates of each of said at least one accelerometer and said patient body frame coordinates to calibrate said at least one accelerometer; and store said at least one rotation matrix in said memory wherein each of said at least one rotation matrix is associated with said at least one accelerometer respectively; and obtain said at least one rotation matrix from said memory and convert incoming acceleration vectors into a reference frame associated with said body of said patient; and calibrate said at least one accelerometer to said device frame coordinates of each of said at least one accelerometer, said patient body frame coordinates and said reference frame associated with said body of said patient; and determine if a potential arrhythmia condition exists based on said peak markers or said signal features; and obtain a heart rate from said peak markers or said signal features; and obtain said at least one motion characteristic from said at least one detection element; and, determine if said peak markers or said signal features from said at least one electrode occur in a time window that includes said at least one motion characteristic over at least one threshold for frequency or amplitude or frequency and amplitude or within range of a pattern if said heart rate is above a fast threshold and if so, mark said potential arrhythmia as incorrect, or otherwise mark said potential arrhythmia as confirmed or determine if said at least one motion characteristic is under a duration threshold if said heart rate is below a slow threshold and if so, mark said potential arrhythmia as confirmed, or otherwise mark said potential arrhythmia as incorrect; and, store incorrect or confirmed or both incorrect and confirmed arrhythmia events in said memory along with said at least one motion characteristic for later analysis.

* * * * *